(12) United States Patent
Esteller

(10) Patent No.: US 12,130,753 B2
(45) Date of Patent: Oct. 29, 2024

(54) METHODS AND SYSTEMS FOR STORAGE, RETRIEVAL, AND VISUALIZATION OF SIGNALS AND SIGNAL FEATURES

(71) Applicant: Boston Scientific Neuromodulation Corporation, Valencia, CA (US)

(72) Inventor: Rosana Esteller, Santa Clarita, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 475 days.

(21) Appl. No.: 17/616,086

(22) PCT Filed: Jul. 24, 2020

(86) PCT No.: PCT/US2020/043570
§ 371 (c)(1),
(2) Date: Dec. 2, 2021

(87) PCT Pub. No.: WO2021/021659
PCT Pub. Date: Feb. 4, 2021

(65) Prior Publication Data
US 2022/0300434 A1 Sep. 22, 2022

Related U.S. Application Data

(60) Provisional application No. 62/879,194, filed on Jul. 26, 2019.

(51) Int. Cl.
*A61N 1/36* (2006.01)
*A61N 1/372* (2006.01)
*G06F 12/123* (2016.01)

(52) U.S. Cl.
CPC ....... *G06F 12/124* (2013.01); *A61N 1/37235* (2013.01); *G06F 2212/171* (2013.01)

(58) Field of Classification Search
CPC .............................. A61N 1/37; A61N 1/37235
See application file for complete search history.

(56) References Cited

U.S. PATENT DOCUMENTS 4,625,730 A * 12/1986 Fountain .............. A61N 1/3925
607/30
5,228,450 A * 7/1993 Sellers ................... A61B 5/303
600/524

(Continued)

FOREIGN PATENT DOCUMENTS

WO 2006/119131 11/2006
WO 2012/155186 11/2012

(Continued)

OTHER PUBLICATIONS

International Search Report and Written Opinion for PCT Application No. PCT/US2020/043570, mailed Oct. 29, 2020.

*Primary Examiner* — Eric D. Bertram
(74) *Attorney, Agent, or Firm* — Branch Partners PLLC; Bruce E. Black

(57) ABSTRACT

An implantable device includes a memory and a processor coupled to the memory and configured to perform actions, including: receiving electrical signals from tissue of a patient; and in response to each of a plurality of triggers, storing a portion of the received electrical signals, occurring after the trigger and extending for a limited duration, in the memory on a first-in-first-out basis. Another an implantable device includes a memory; and a processor coupled to the memory and configured to perform actions, including: receiving electrical signals from tissue of a patient; and in response to each of a plurality of triggers, determining at least one feature of the received electrical signals; and storing the at least one feature in the memory on a first-in-first-out basis.

18 Claims, 7 Drawing Sheets

(56) References Cited

U.S. PATENT DOCUMENTS

| | | | |
|---|---|---|---|
| 5,697,958 A | 12/1997 | Paul et al. | |
| 5,702,429 A | 12/1997 | King | |
| 5,902,236 A | 5/1999 | Iverson | |
| 5,902,249 A | 5/1999 | Fyster | |
| 5,913,882 A | 6/1999 | King | |
| 6,061,593 A * | 5/2000 | Fischell | G16H 20/40 |
| | | | 600/544 |
| 6,181,969 B1 | 1/2001 | Gord | |
| 6,347,245 B1 * | 2/2002 | Lee | A61B 5/7203 |
| | | | 600/509 |
| 6,516,227 B1 | 2/2003 | Meadows et al. | |
| 6,560,490 B2 | 5/2003 | Grill et al. | |
| 6,599,242 B1 * | 7/2003 | Splett | A61B 5/7232 |
| | | | 345/440.1 |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,895,280 B2 | 5/2005 | Meadows et al. | |
| 7,024,247 B2 | 4/2006 | Gliner et al. | |
| 7,136,695 B2 | 11/2006 | Pless et al. | |
| 7,244,150 B1 | 7/2007 | Brase et al. | |
| 7,424,322 B2 | 9/2008 | Lombardi et al. | |
| 7,437,193 B2 | 10/2008 | Parramon et al. | |
| 7,450,992 B1 | 11/2008 | Cameron | |
| 7,450,997 B1 | 11/2008 | Pianca et al. | |
| 7,603,179 B1 | 10/2009 | Grandhe | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,255,057 B2 | 8/2012 | Fang et al. | |
| 8,271,094 B1 | 9/2012 | Moffitt et al. | |
| 8,295,944 B2 | 10/2012 | Howard et al. | |
| 8,335,664 B2 | 12/2012 | Eberle | |
| 8,352,030 B2 | 1/2013 | Denison | |
| 8,364,278 B2 | 1/2013 | Pianca et al. | |
| 8,391,985 B2 | 3/2013 | McDonald | |
| 8,606,362 B2 | 12/2013 | He et al. | |
| 8,620,436 B2 | 12/2013 | Parramon et al. | |
| 8,688,235 B1 | 4/2014 | Pianca et al. | |
| 8,768,453 B2 | 7/2014 | Parramon et al. | |
| 8,805,498 B1 * | 8/2014 | Fischell | A61N 1/37247 |
| | | | 607/9 |
| 9,044,155 B2 | 6/2015 | Strahl | |
| 9,061,140 B2 | 6/2015 | Shi et al. | |
| 9,113,801 B2 | 8/2015 | DiLorenzo | |
| 9,119,964 B2 | 9/2015 | Marnfeldt | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bomzin et al. | |
| 9,381,356 B2 | 7/2016 | Parker et al. | |
| 9,386,934 B2 | 7/2016 | Parker et al. | |
| 9,399,132 B2 | 7/2016 | Parramon et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 2002/0156513 A1 | 10/2002 | Borkan | |
| 2003/0139781 A1 | 7/2003 | Bradley et al. | |
| 2005/0113705 A1 * | 5/2005 | Fischell | A61B 5/366 |
| | | | 600/515 |
| 2005/0246004 A1 | 11/2005 | Cameron et al. | |
| 2006/0229523 A1 * | 10/2006 | Barr | A61B 5/332 |
| | | | 600/509 |
| 2006/0229525 A1 * | 10/2006 | Barr | A61B 5/308 |
| | | | 600/523 |
| 2007/0150036 A1 | 6/2007 | Anderson | |
| 2007/0213629 A1 | 9/2007 | Greene | |
| 2008/0146894 A1 | 6/2008 | Bulkes et al. | |
| 2009/0187222 A1 | 7/2009 | Barker | |
| 2009/0216141 A1 * | 8/2009 | Fischell | A61B 5/0031 |
| | | | 600/509 |
| 2009/0276021 A1 | 11/2009 | Meadows et al. | |
| 2010/0076535 A1 | 3/2010 | Pianca et al. | |
| 2010/0099995 A1 * | 4/2010 | Lian | A61N 1/3702 |
| | | | 600/509 |
| 2010/0114224 A1 | 5/2010 | Krause et al. | |
| 2010/0268298 A1 | 10/2010 | Moffitt et al. | |
| 2010/0305642 A1 * | 12/2010 | Dong | A61N 1/3702 |
| | | | 607/17 |
| 2010/0331916 A1 | 12/2010 | Parramon et al. | |
| 2011/0004267 A1 | 1/2011 | Meadows | |
| 2011/0005069 A1 | 1/2011 | Pianca | |
| 2011/0078900 A1 | 4/2011 | Pianca et al. | |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0197602 A1 | 8/2013 | Pianca et al. | |
| 2013/0289665 A1 | 10/2013 | Marnfeldt et al. | |
| 2014/0031901 A1 | 1/2014 | Zhu et al. | |
| 2014/0194772 A1 | 7/2014 | Single et al. | |
| 2014/0236042 A1 | 8/2014 | Parker et al. | |
| 2014/0243926 A1 | 8/2014 | Carcieri | |
| 2014/0276707 A1 | 9/2014 | Jaax | |
| 2014/0277282 A1 | 9/2014 | Jaax | |
| 2014/0296737 A1 | 10/2014 | Parker et al. | |
| 2015/0018699 A1 | 1/2015 | Zeng et al. | |
| 2015/0119751 A1 | 4/2015 | Stanslaski et al. | |
| 2015/0157861 A1 | 6/2015 | Aghassian | |
| 2015/0282725 A1 | 10/2015 | Single | |
| 2015/0313487 A1 | 11/2015 | Single et al. | |
| 2015/0360038 A1 | 12/2015 | Zottola et al. | |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0049345 A1 | 2/2017 | Single | |
| 2017/0071490 A1 | 3/2017 | Parker et al. | |
| 2017/0113046 A1 | 4/2017 | Fried et al. | |
| 2017/0135624 A1 | 5/2017 | Parker | |
| 2017/0136243 A1 | 5/2017 | Lee et al. | |
| 2017/0157410 A1 | 6/2017 | Moffitt et al. | |
| 2017/0173335 A1 | 6/2017 | Min et al. | |
| 2017/0216587 A1 | 8/2017 | Parker | |
| 2017/0259065 A1 | 9/2017 | Baru et al. | |
| 2017/0281958 A1 | 10/2017 | Serrano Carmona et al. | |
| 2017/0296823 A1 | 10/2017 | Hershey et al. | |
| 2017/0361101 A1 | 12/2017 | Single | |
| 2018/0028083 A1 * | 2/2018 | Greenhut | A61N 1/3956 |
| 2018/0071513 A1 | 3/2018 | Weiss et al. | |
| 2018/0071520 A1 | 3/2018 | Weerakoon et al. | |
| 2018/0071527 A1 | 3/2018 | Feldman et al. | |
| 2018/0071530 A1 | 3/2018 | Giftakis et al. | |
| 2018/0078769 A1 | 3/2018 | Dinsmoor et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |

(56) References Cited

U.S. PATENT DOCUMENTS

| | | | |
|---|---|---|---|
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2018/0289967 A1 | 10/2018 | Bokil | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |
| 2019/0275331 A1 | 9/2019 | Zhu | |
| 2019/0290900 A1 | 9/2019 | Esteller et al. | |
| 2019/0298992 A1 | 10/2019 | Zhang et al. | |
| 2019/0299006 A1 | 10/2019 | Marnfeldt | |
| 2019/0366094 A1 | 12/2019 | Esteller et al. | |
| 2020/0155019 A1 | 5/2020 | Esteller et al. | |
| 2020/0305745 A1 | 10/2020 | Wagenbach et al. | |
| 2020/0376263 A1 | 12/2020 | Zhu | |
| 2020/0398057 A1 | 12/2020 | Esteller et al. | |
| 2021/0023374 A1 | 1/2021 | Block et al. | |
| 2021/0402190 A1* | 12/2021 | Zhang | A61B 5/4836 |

FOREIGN PATENT DOCUMENTS

| | | |
|---|---|---|
| WO | 2015/077362 | 5/2015 |
| WO | 2017/100866 | 6/2017 |
| WO | 2017/173493 | 10/2017 |
| WO | 2017/210352 | 12/2017 |
| WO | 2017/219096 | 12/2017 |

\* cited by examiner

METHODS AND SYSTEMS FOR STORAGE, RETRIEVAL, AND VISUALIZATION OF SIGNALS AND SIGNAL FEATURES

CROSS-REFERENCE TO RELATED APPLICATIONS

This application is the U.S. national stage application of PCT Application No. PCT/US2020/043570, filed Jul. 24, 2020, which claims the benefit under 35 U.S.C. § 119 (e) of U.S. Provisional Patent Application Ser. No. 62/879,194, filed Jul. 26, 2019, both of which are incorporated herein by reference.

FIELD

The present disclosure is directed to the area of implantable electrical stimulation systems and methods of making and using the systems. The present disclosure is also directed to methods and systems for storing, retrieving, and visualizing signals and signal features using an implantable pulse generator.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is an implantable device that includes a memory and a processor coupled to the memory and configured to perform actions, including: receiving electrical signals from tissue of a patient; and in response to each of a plurality of triggers, storing a portion of the received electrical signals, occurring after the trigger and extending for a limited duration, in the memory on a first-in-first-out basis.

Another aspect is a method of storing electrical signals from tissue of a patient that includes: receiving electrical signals from tissue of a patient; and in response to each of a plurality of triggers, storing in the memory of an implantable device a portion of the received electrical signals, occurring after the trigger and extending for a limited duration, on a first-in-first-out basis.

In at least some aspects of the implantable device or method, the trigger includes a user-initiated trigger or a scheduled trigger. In at least some aspects, the trigger includes either 1) the electrical signals exceeding a threshold condition or 2) the electrical signals meeting a threshold condition. In at least some aspects, the trigger includes the electrical signals failing to meet a threshold condition.

In at least some aspects, the limited duration is predetermined. In at least some aspects, the limited duration is divided into at least a first segment and a second. In at least some aspects, storing the portion of the received electrical signals includes storing a first portion of the received electrical signals during the first segment at a first sampling rate and storing a second portion of the received electrical signals during the second segment at a second sampling rate that is lower than the first sampling rate.

In at least some aspects, the actions further include storing the received electrical signals in a pre-trigger buffer of the memory and, in response to the trigger, storing at least a portion of the pre-trigger buffer in the memory with the stored portion of the received electrical signals occurring after the trigger. In at least some aspects, the implantable device is an implantable pulse generator, the implantable device further including a lead including electrodes, wherein receiving electrical signals includes receiving electrical signals through at least one electrode of the lead.

Another aspect is an implantable device that includes a memory; and a processor coupled to the memory and configured to perform actions, including: receiving electrical signals from tissue of a patient; and in response to each of a plurality of triggers, determining at least one feature of the received electrical signals; and storing the at least one feature in the memory on a first-in-first-out basis.

A further aspect is a method of storing electrical signals from tissue of a patient that includes: receiving electrical signals from tissue of a patient; and in response to each of a plurality of triggers, determining at least one feature of the received electrical signals; and storing the at least one feature in a memory of an implantable device on a first-in-first-out basis.

In at least some aspects of the implantable device or the method, the trigger includes a user-initiated trigger or a scheduled trigger. In at least some aspects, the trigger includes either 1) the electrical signals exceeding a threshold condition or 2) the electrical signals meeting a threshold condition. In at least some aspects, the trigger includes the electrical signals failing to meet a threshold condition.

In at least some aspects, the actions further include in response to each of the plurality of triggers, storing a portion of the received electrical signals, occurring after the trigger and extending for a limited duration, in the memory on a first-in-first-out basis. In at least some aspects, the limited duration is divided into at least a first segment and a second segment. In at least some aspects, storing the portion of the received electrical signals includes storing a first portion of the received electrical signals during the first segment at a first sampling rate and storing a second portion of the received electrical signals during the second segment at a second sampling rate that is lower than, or otherwise different from, the first sampling rate.

In at least some aspects, the actions further include storing the received electrical signals in a pre-trigger buffer of the memory and, in response to the trigger, storing at least a portion of the pre-trigger buffer in the memory with the stored portion of the received electrical signals occurring after the trigger. In at least some aspects, the implantable device is an implantable pulse generator, the implantable device further including a lead including electrodes, wherein receiving electrical signals includes receiving electrical signals through at least one electrode of the lead.

Another aspect is a system that includes any of the implantable devices described above and a programming device configured for user programming of one or more parameters or triggers relating the storage in the memory of the implantable device. The programming device may also be configured for retrieving stored electrical signals or features from the implantable device or visualizing the stored electrical signals or features.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable electrical stimulation systems and methods of making and using the systems. The present disclosure is also directed to methods and systems for storing, retrieving, and visualizing signals and signal features using an implantable pulse generator.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for spinal cord stimulation, but it will be understood that any of the leads can be used for applications other than spinal cord stimulation, including deep brain stimulation, peripheral nerve stimulation, dorsal root ganglion stimulation, sacral nerve stimulation, or stimulation of other nerves, muscles, and tissues.

Figure 1:
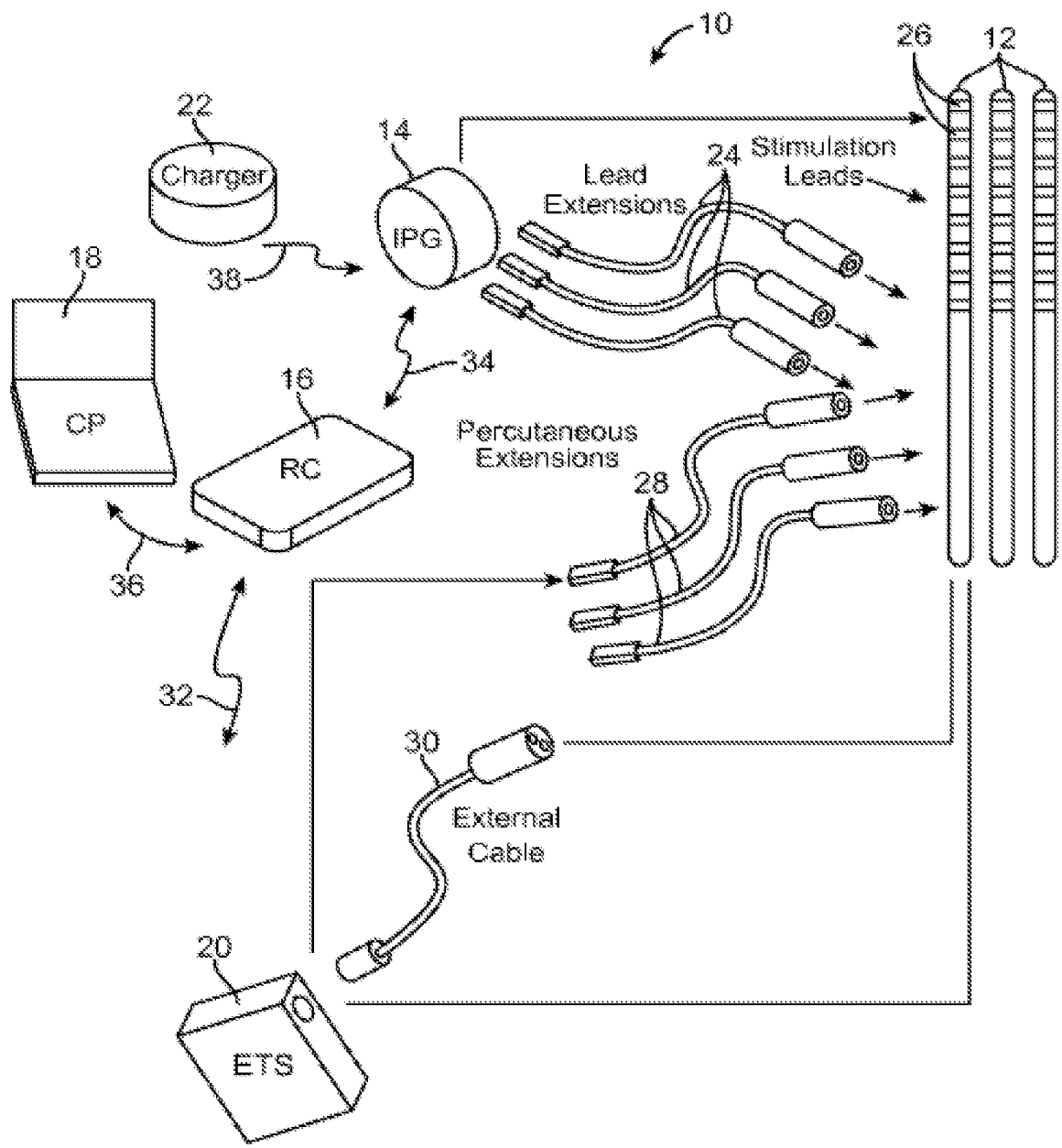
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth, Wi-Fi, or any other suitable wireless communications) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18). In at least some embodiments, the CP 18 or RC 16 can be a mobile device, such as a mobile phone.

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Figure 2:
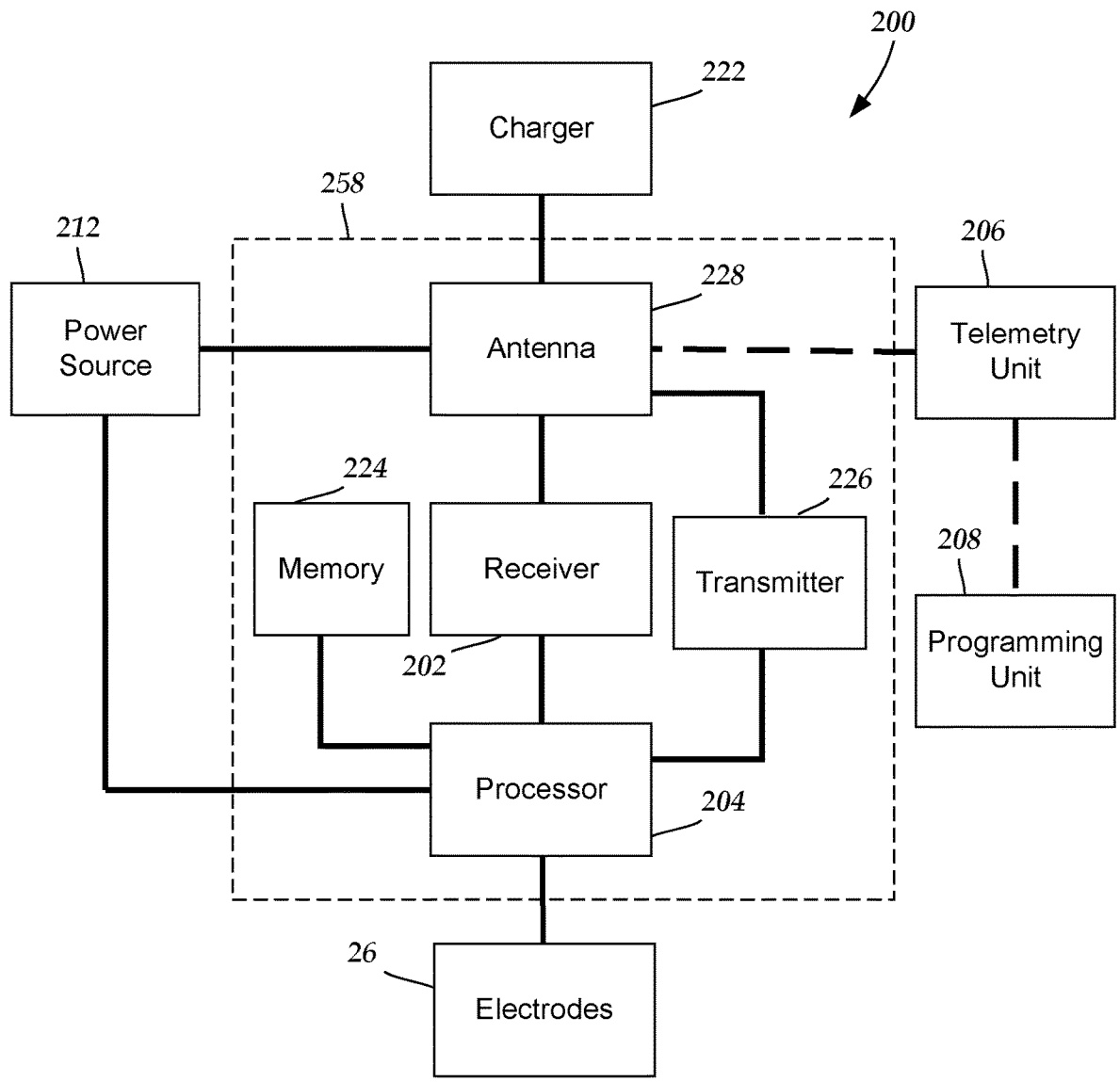
FIG. 2 is a schematic overview of one embodiment of components of a stimulation system, including an electronic subassembly disposed within a control module such as an implantable pulse generator (IPG) or external trial stimulator (ETS)

FIG. 2 is a schematic overview of one embodiment of components of an electrical stimulation system 200 (which may be the same or different from the electrical stimulation system 10, but which is broken down into components in a different way.). It will be understood that the electrical stimulation system can include more, fewer, or different components and can have a variety of different configurations including those configurations disclosed in the stimulator references cited herein.

The electrical stimulation system 200 includes an electronic subassembly 258 and power source 212 disposed within the IPG 14 or ETS 20 (FIG. 1) each of which may also be considered a control module. Some of the components (for example, a power source 212, an antenna 228, a receiver 202, a memory 224, and a processor 204) of the electrical stimulation system can be positioned on one or more circuit boards or similar carriers within a sealed housing of an implantable pulse generator (see e.g., 14 in FIG. 1), if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the antenna 228 or a secondary antenna. The external power source can be in a device that is mounted on the skin of the user or in a unit that is provided near the user on a permanent or periodic basis.

If the power source 212 is a rechargeable battery, the battery may be recharged using the charger 22 (FIG. 1) using the optional antenna 228, if desired. Power can be provided to the battery for recharging by inductively coupling the battery through the antenna to a charger 222 external to the user. Examples of such arrangements can be found in the references identified above. The electronic subassembly 258, processor 204, memory 224, receiver 202, transmitter 226, antenna 228, and, optionally, the power source 212 can be disposed within or on a control module (e.g., the IPG 14 or the ETS 20 of FIG. 1).

In one embodiment, electrical stimulation signals are emitted by the electrodes 26 to stimulate nerve fibers, muscle fibers, or other body tissues near the electrical stimulation system. The processor 204 is generally included to control the timing and electrical characteristics of the electrical stimulation system. For example, the processor 204 can, if desired, control one or more of the timing, frequency, strength, duration, and waveform of the pulses. In addition, the processor 204 can select which electrodes can be used to provide stimulation, if desired. In some embodiments, the processor 204 selects which electrode(s) are cathodes and which electrode(s) are anodes. In some embodiments, the processor 204 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 208 (such as the RC 16 or CP 18) that, for example, allows modification of pulse characteristics. In the illustrated embodiment, the processor 204 is coupled to a receiver 202 which, in turn, is coupled to the optional antenna 228. This allows the processor 204 to receive instructions from an external source (for example, the RC 16 or CP 18) to, for example, direct the pulse characteristics and the selection of electrodes, if desired.

Any suitable memory 224 can be used. The memory 224 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

In one embodiment, the antenna 228 is capable of receiving signals (e.g., RF signals) from an external telemetry unit 206 which is programmed by the programming unit 208. (The external telemetry unit 206 and programming unit 208 can be, for example, the RC 16 or CP 18 of FIG. 1.) The programming unit 208 can be external to, or part of, the telemetry unit 206. The telemetry unit 206 can be a device that is worn on the skin of the user or can be carried by the user and can have a form similar to a pager, cellular phone, or remote control, if desired. As another alternative, the telemetry unit 206 may not be worn or carried by the user but may only be available at a home station or at a clinician's office. The programming unit 208 can be any unit that can provide information to the telemetry unit 206 for transmission to the electrical stimulation system 200. The programming unit 208 can be part of the telemetry unit 206 or can provide signals or information to the telemetry unit 206 via a wireless or wired connection. One example of a suitable programming unit is a computer operated by the user or clinician to send signals to the telemetry unit 206.

The signals sent to the processor 204 via the antenna 228 and the receiver 202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 200 to cease operation, to start operation, to start charging the battery, or to stop charging the battery. In other embodiments, the stimulation system does not include the antenna 228 or receiver 202 and the processor 204 operates as programmed.

In at least some embodiments, the electrical stimulation system 200 may include a transmitter 226 coupled to the processor 204 and the antenna 228 for transmitting signals back to the telemetry unit 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

In addition to delivering electrical stimulation, the electrodes 26 of the lead(s) 12 (FIG. 1) can be used to receive or sense electrical signals from the surrounding tissue, as well as provide stimulation to the tissue. Examples of such electrical signals include, but are not limited to, electrospinogram (ESG), evoked composite action potential (ECAP), evoke response, electroencephalogram (EEG), intracranial electroencephalogram (iEEG), stereoelectroencephalogram (SEEG), electromyogram (EMG), electroneurogram (ENG), or peripheral nerve signals, or the like or any combination thereof. In some embodiments, in addition to, or as an alternative to, the electrodes 26, the lead (or a separate lead) can include recording or sensor electrodes that are primarily used for receiving or sensing the electrical signals. Examples of methods and systems for sensing electrical signals can be found in U.S. Patent Application Publications Nos. 2014/0243926; 2014/0276707; and 2014/0277282 and U.S. Provisional Patent Applications Ser. Nos. 62/854,514 and 62/864,195, all of which are incorporated herein by reference in their entireties.

Knowledge and characterization of the local stimulation environment around a lead or the electrodes of a lead can provide useful information. For example, information regarding the impedance, conductivity, or capacitance of the tissue near the lead or electrodes, stimulation induced voltage distribution, current intensity, or charging and discharging characteristics, changes associated with heartbeat and respiration, changes associated with postural position or intensity of physical activities, changes associated with use of medications and dosing of those medications affecting the characteristics of the signals sensed, as well as other electrical characteristics of the tissue, can be determined. Changes in the local stimulation environment may indicate the development, presence, or alterations in scar tissue or fluid around the lead, or electrode, may indicate thickness of fat tissue, thickness of cerebral spinal fluid (for spinal cord stimulation systems), may indicate lead position in the spinal canal, may indicate the relative lead position or electrode position in a multiple lead array, may be used to indicate, infer or determine patient posture or activity, or the like or any combination thereof.

In at least some embodiments, the electrodes of the lead(s) can be used to sense electrical signals or local electrical characteristics of the environment around the lead(s) and electrodes prior to, during, or between electrical pulses delivered by the lead(s) (which can be, for example, therapeutic stimulation pulses, supra- or sub-perception pulses (pulses perceived or not perceived by the person, respectively), dedicated sensing pulses, charge-balancing pulses or other electrical pulses or combinations thereof) It will be understood that the electrodes of the lead(s) can also be used to sense electrical signals or local electrical characteristics in the absence of any electrical pulses delivered from the lead(s).

Similar to having multiple channels for delivery of the electrical stimulation, in at least some embodiments, the IPG or system can have multiple sensing channels for receiving electrical signals or identifying local electrical characteristics. In at least some embodiments, each sensing channel can be identified by the electrode(s) used for the sensing. In some embodiments, a sensing channel may be defined by utilizing two or more electrode(s) (e.g., at least one cathode and at least one anode) from one or more leads. This sensing channel may provide a differential signal (when two electrodes are subtracted) or composed signal (when two or more electrodes are combined). In some embodiments, sensing channels may be defined in a referential mode, by a single electrode (or multiple electrodes of the same polarity) on the lead with respect to a remote reference electrode, such as the case of the IPG or an external electrode. This sensing channel may provide a referential signal.

As described herein, an implantable system capable of sensing, displaying, and storing electrical signals obtained from the patient benefits from a system and methodology to reduce or minimize signal losses and utilize memory storage intelligently. The collection and storage of ESG signals will be used herein as an example, but it will be recognized that the arrangements and methods described herein can be used with any electrical signals including, but not limited to, those listed above. The storage of such signals can be beneficial to the treatment of disorders or conditions such as, for example, chronic pain, Parkinson's disease, Alzheimer's disease, painful peripheral neuropathy, multiple sclerosis, cardiac conditions, and the like.

Figure 3:
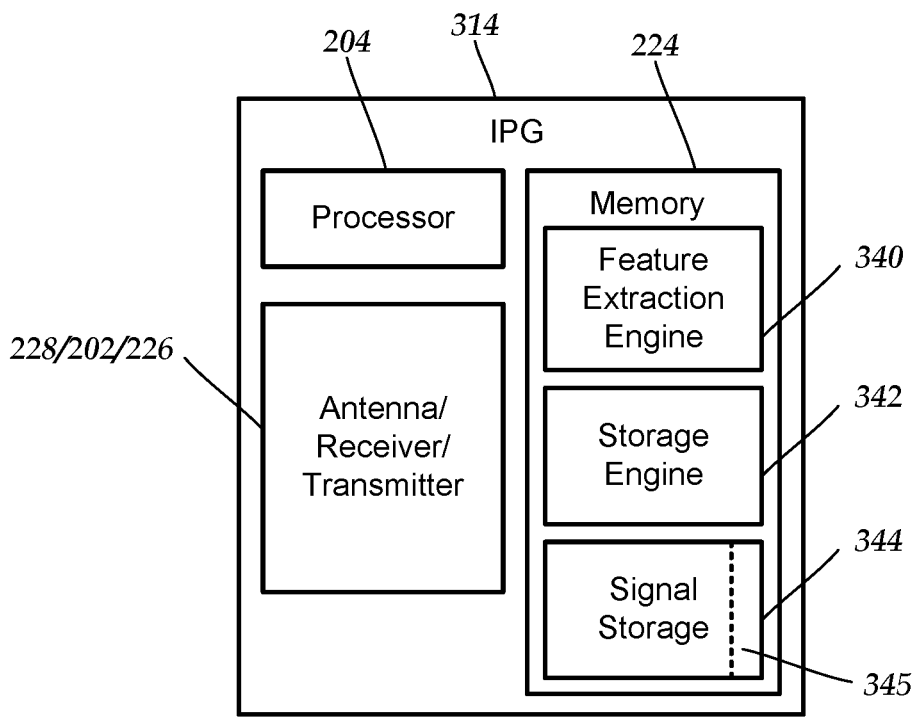
FIG. 3 is a schematic overview of one embodiment of select components of an implantable device, such as an IPG.

FIG. 3 illustrates some components of one embodiment of an IPG 314 (or other implantable device) that includes, but is not limited to, a processor 204, memory 224, and an antenna/receiver/transmitter 228/202/226 (as illustrated in FIG. 2). The memory 224 can include instructions for a feature extraction engine 340 and a storage engine 342 (which may be combined into a single engine) which can be instantiated in the processor 204. The memory 224 also includes space for electrical signal storage 344.

Figure 4:
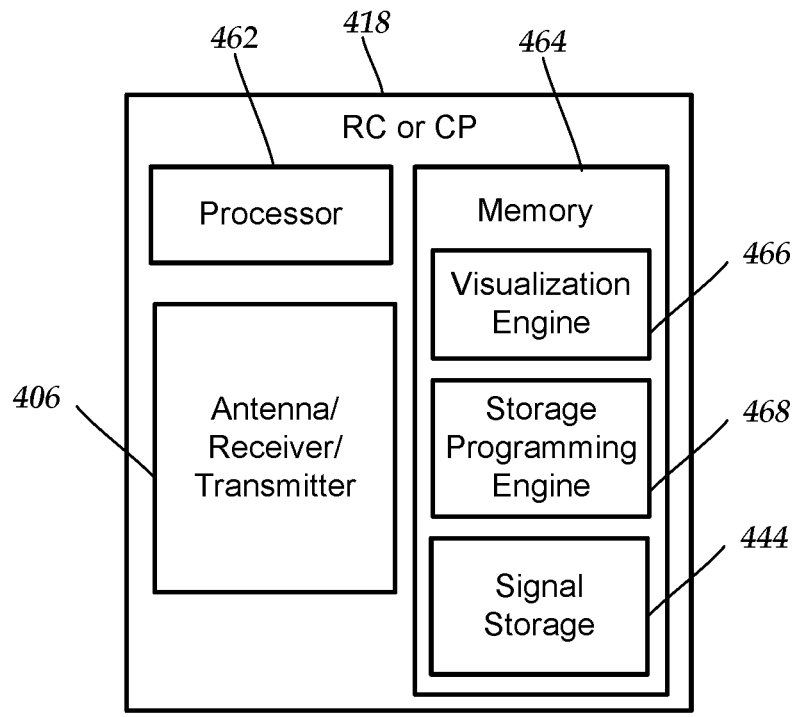
FIG. 4 is a schematic overview of one embodiment of select components of a remote control (RC) or clinician programmer (CP) or other programming device.

FIG. 4 illustrates some components of one embodiment of a RC or CP 418 (or other programming device) that includes, but is not limited to, a processor 462, memory 464, and an antenna/receiver/transmitter 406 (such as the telemetry unit 206 illustrated in FIG. 2). The processor 462 and memory 464 can utilize the same features and design considerations described above for processor 204 and memory 224 in FIGS. 2 and 3. The memory 464 can include instructions for a visualization engine 466 and a storage programming engine 468 (which may be combined into a single engine) which can be instantiated in the processor 462. The memory 464 also includes space for electrical signal storage 444. In some embodiments, the feature extraction engine 340 or the storage engine 342 can reside in the RC or CP 418 or the storage programming engine 468 or visualization engine 466 can reside in the memory 224 of the IPG 314.

The storage engine 342 is configured to enable and enhance the storage of the electrical signals or features extracted from the electrical signals (or any combination thereof) in the signal storage 344 of the IPG 314. In at least some embodiments, the storage engine 342 may also direct the transmission of the electrical signals or features to the RC or CP 418 using the antenna/receive/transmitter 228/202/226. The storage engine 342 is provided to direct and manage storage of the electrical signals or features along with additional metadata, tags, or labels that can be useful for review or analysis.

The feature extraction engine 340 of the IPG, if present, can be used to analyze the electrical signals to identify features of the electrical signals. Examples of such features include, but are not limited to, an area under curve of the electrical signal; a range of an amplitude of the curve in a defined time window; a length of the curve of the electrical signal; an energy content of the electrical signal; a range of a derivative of the electrical signal in a predefined time window; a time delay of a specified signal peak of the electrical signal; power of the electrical signal in a predefined frequency band; variation of a frequency peak with highest energy in the electrical signal in a predefined frequency band; coherence changes in the electrical signal; a quality factor for a specified signal peak of the electrical signal in a predefined time window; or full width at half amplitude (FWHM) for a specified signal peak of the electrical signal in a predefined time window; mutual information in the electrical signals; entropy of the electrical signal; spectral entropy of the electrical signal; a standard deviation of any of the previous metrics; or the like or any combination thereof. The features may be evaluated in the frequency domain or time domain.

The IPG 314 may have limited space in the memory 224 for storage of electrical signals or features. Moreover, storage of electrical signals or features may utilize the limited power available from the power source 212 (FIG. 2). Thus, it is useful to manage the storage of the electrical signals as described herein to control the use of the available signal storage 344 and conserve power from the power source 212. In at least some embodiments, the limited storage on the IPG 314 may be for temporary storage until the electrical signals or features can be uploaded to the RC or CP. In at least some embodiments, the storage engine 342 manages storage of the electrical signals or features in the signal storage 344 of the memory 224 on a first-in-first-out (FIFO) basis so that older information is erased, removed, or written-over first.

In at least some embodiments, the storage engine 342 is configured to only store the electrical signals or features in response to a trigger. Examples of triggers include, but are not limited to, user-initiated triggers, scheduled triggers, visualization triggers, and threshold triggers. A user-initiated trigger can be, for example, a signal from the RC or CP, initiated by the user, directing the IPG 314 to store the electrical signals or features. A scheduled trigger can be scheduled by the user on the RC or CP or can be scheduled by the system. The scheduled trigger can be, for example, a trigger that occurs at a regular or irregular interval (for example, every 10, 15, or 30 minutes or every 1, 2, 4, 6, or 12 hours or every day) or can be scheduled for a particular time each day, hour, a particular day and time of every week, or a particular date and time of every month, or the like. A visualization trigger can be similar to a user-initiated trigger in that the storage of the electrical signals or features is initiated in response to a user (for example, patient or clinician). In the case of a visualization trigger, the trigger includes initiated while the user is visualizing the current electrical signals or features on the RC or CP and the user decides to trigger the storage.

A threshold trigger can occur when the electrical signals or features 1) exceed a threshold, 2) meet a threshold, or 3) fail to exceed a threshold. For example, the threshold trigger may occur when the electrical signals or features meet or exceed an amplitude or magnitude threshold (which may indicate, for example, that something out of the ordinary has occurred) or when the electrical signals fail to meet an amplitude or magnitude threshold (which may indicate, for example, a device issue or patient issue.) As another example, the threshold trigger may occur when the features meet, exceed, or fail to exceed an acceleration threshold (e.g., a rate of change threshold). For example, in the case of spinal cord stimulators, if the patient is walking, coughing, laughing, inhaling or exhaling, the features extracted from the sensed electrical signals may change faster over a broader or smaller range of values, within a short period of time, which can be detected. In at least some embodiments, a threshold is based on the rate of change of the feature. For example, a threshold can be the change of a feature over a particular time interval divided by the time interval (e.g., $\Delta$feature/$\Delta$time). Other trigger threshold or criteria can be used based on any suitable logical combination (e.g., AND, OR, or the like) of features and thresholds, for example: (feature 1<threshold1) AND (feature 2<threshold2) OR (acceleration feature1>accelerationThreshold1) then trigger storage.

In at least some embodiments, in addition to one or more triggers, the storage engine 342 utilizes one or more parameters to determine what portion of the electrical signals or which features to store. The parameters can include, but are not limited to, one or more of the following: the type of event or trigger that initiates storage of the electrical signals or features; the type of features to be stored; the length of time (referred to herein as a "segment") to be stored; the number of segments to store for each electrical signal; the number of electrical signals (e.g., the number of signal channels) to store or for which features are to be stored; filtering or gain applied to the electrical signals; the sampling rate or amplitude range for the electrical signal; and the like or any combination thereof. In addition, the storage engine 342 can record information about the electrical signals or features including, but not limited to, the selection of which of the electrodes define a signal channel; the selection of which of the electrodes is the reference electrode; the sensing mode (e.g., referential or differential); the polarity of the electrodes; and the like or any combination thereof. The storage engine 342 can also store a date/time stamp with the electrical signals or features.

Figure 5:
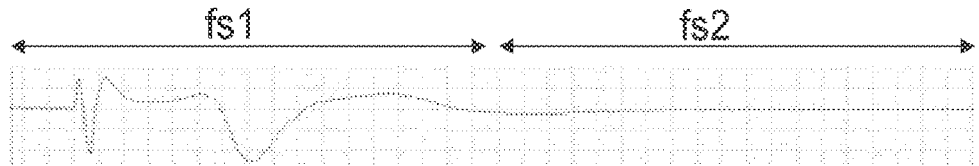
FIG. 5 is an illustration of an electrical signal divided into two segments.

In at least some embodiments, when more than one consecutive segment of an electrical signal is stored, the segments can be stored with different sampling rates or different amplitude ranges. For example, as illustrated in FIG. 5, a first segment ("fs1" in FIG. 5) and subsequent second segment ("fs2" in FIG. 5) can be stored using different sampling rates. For example, the sampling rate or amplitude range (of both) of the second segment can be smaller than for the first segment because the second segment is likely to have weaker variations and likely to have a relatively smooth tail after the first segment so using a lower sampling rate or amplitude range likely will not result in appreciable information loss.

The storage engine 342 may also store labels that are associated with the electrical signals or features. The labels may be designated by the user using the RC or CP or other device or may be determined or estimated by analysis of the electrical signals. Examples of labels for spinal cord stimulation include, but are not limed to, labels regarding patient activity or posture at the time that the electrical signals are sensed. Examples of labels include, but are not limited to, reclined, lying left, lying right, lying on back (supine), lying on front (prone), sitting >90, sitting <90, standing, other, or the like.

In at least some embodiments, a portion of the electrical signals prior to the trigger may be stored. In at least some embodiments, the storage engine 342 may designate part of the memory 224 of signal storage 344 as a pre-trigger buffer 345 to store the electrical signals during recordation so that, if a trigger occurs, the portion of the electrical signals prior to the trigger can be stored with the post-trigger electrical signals or analyzed for features.

Figure 6:
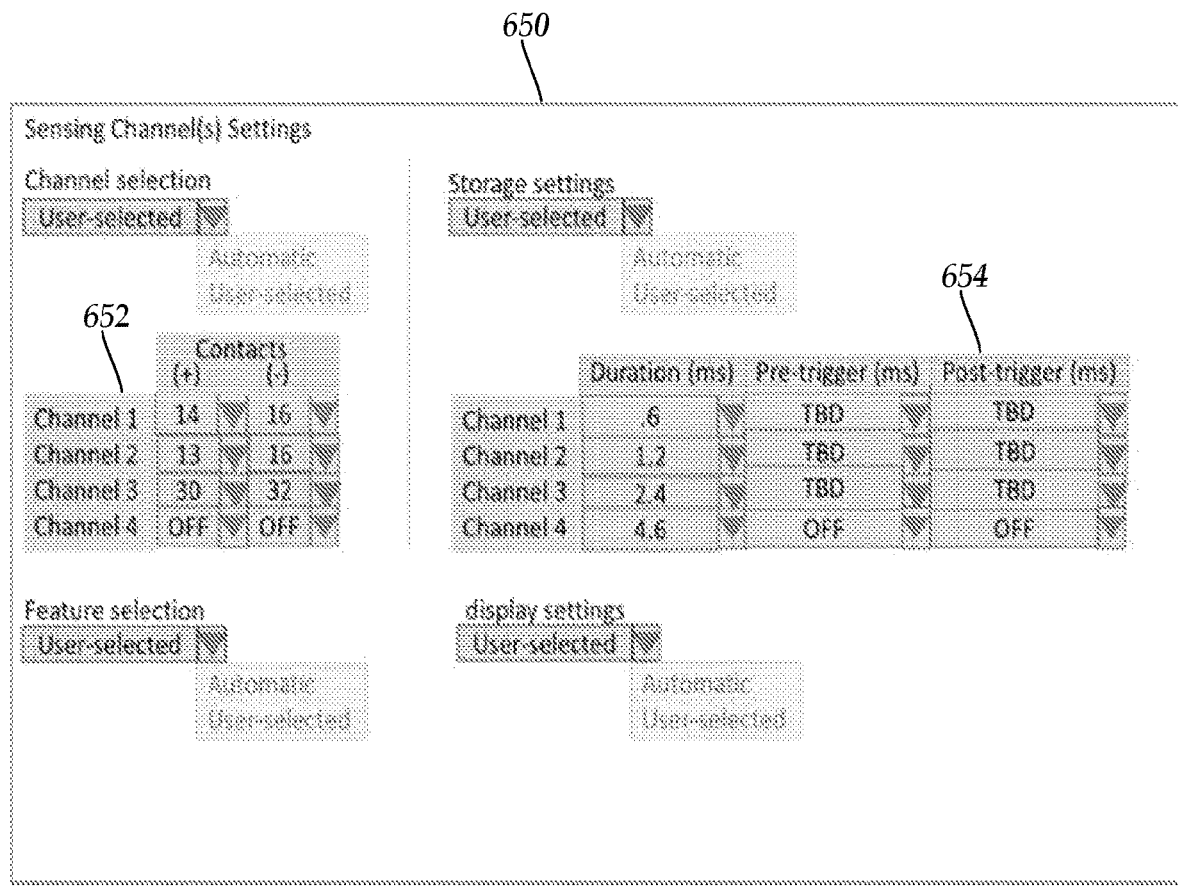
FIG. 6 illustrates one embodiment of a user interface for a storage programming engine.

The storage programming engine 468 of the RC or CP 418 can be used to program the parameters and labels utilized by the storage engine 342. FIG. 6 illustrates one embodiment of a user interface 650 for use by the storage programming engine 468 to receive parameters and labels. (In FIGS. 6 and 7, examples of menu choices are illustrated next to the menu-selection arrow.) This is one example of a user interface, but it will be understood that other user interfaces can be rearranged and include more or fewer regions then the user interface 650. In region 652, a user can select the number of channels (for example, in FIG. 6 three channels are utilized and a fourth channel is turned off), which electrodes ("Contacts" in FIG. 6) are used, and which polarity each contact has. In region 654, the user can select how long ("Duration" in FIG. 6) that the electrical signal will be recorded (or evaluated for features) and whether to store any portion of the electrical signal prior to the trigger or after the initial recording. Other regions may provide for features selection or display settings, as illustrated in FIG. 6.

Figure 7:
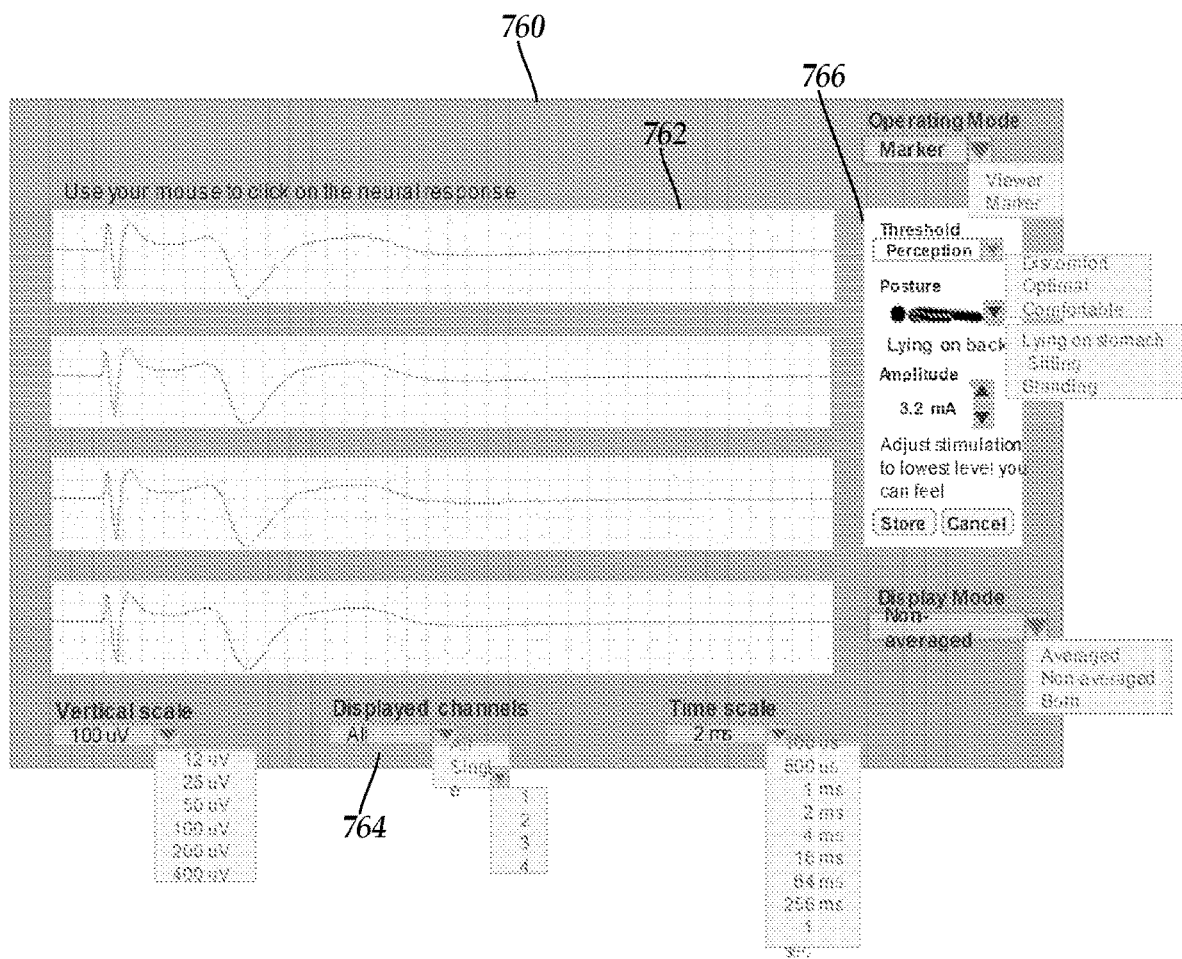
FIG. 7 illustrates one embodiment of a user interface for a visualization engine.

The visualization engine 466 of the RC or CP 418 can be used to observe or review electrical signals or features in a user interface 760, as illustrated in FIG. 7. The user interface 760 of the visualization engine 466 may also allow a user to define parameters or labels utilized by the storage programming engine 468 or storage engine 342. FIG. 7 illustrates one example of a user interface, but it will be understood that other user interfaces can be rearranged and include more or fewer regions then the user interface 760. In region 762, one or more representations of the electrical signals or features of the electrical signals are presented. In region 764, one or more display parameters, such as vertical scale, displayed channels, and time scale, can be selected. In some embodiments, the selections only apply to the visualization, but in other embodiments, the selections may also be provided to the storage engine 342 and determine how the electrical signals or features are stored. In another section 766, parameters or labels can be defined such as the patient's perception of stimulus (labeled "Threshold"), neural threshold, testing threshold, lowest comfortable threshold, maximum comfortable threshold, discomfort threshold, a label for posture or activity, or a stimulation amplitude.

Figure 8:
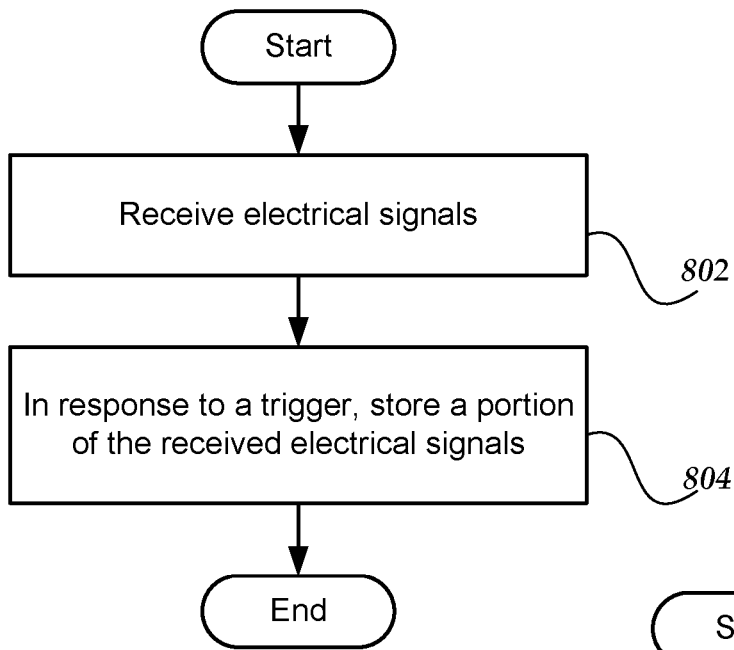
FIG. 8 is a flowchart of one embodiment of a method of storing electrical signals on an implantable device.

FIG. 8 is a flowchart of one embodiment of a method of storing electrical signals on an implantable device, such as IPG 14 (FIG. 1). In step 802, electrical signals from the tissue of a patient are received by the implantable device. In at least some embodiments, the electrical signals are sensed using electrodes on a lead coupled the implantable device, although other sensing arrangements can also be used. The electrical signals may be sensed continuously or intermittently or in response to a trigger.

In step 804, in response to a trigger, a portion of the received electrical signals is stored. That portion can be, for example, the portion of the electrical signals occurring after the trigger and extending for a limited duration (for example, for a predetermined duration.) The portion of the receive electrical signals that is stored may also be selected to be the electrical signals obtained through one or more predetermined channels. The trigger can be any suitable trigger including the user-initiated trigger, scheduled trigger, visualization trigger, or threshold trigger described above. The portion of the received electrical signals may be stored according to one or more predetermined parameters, as described above. In some embodiments, the storage is performed on a first-in-first-out basis. In at least some embodiments, some or all of the steps can be performed by a storage engine of the implantable device.

Figure 9:
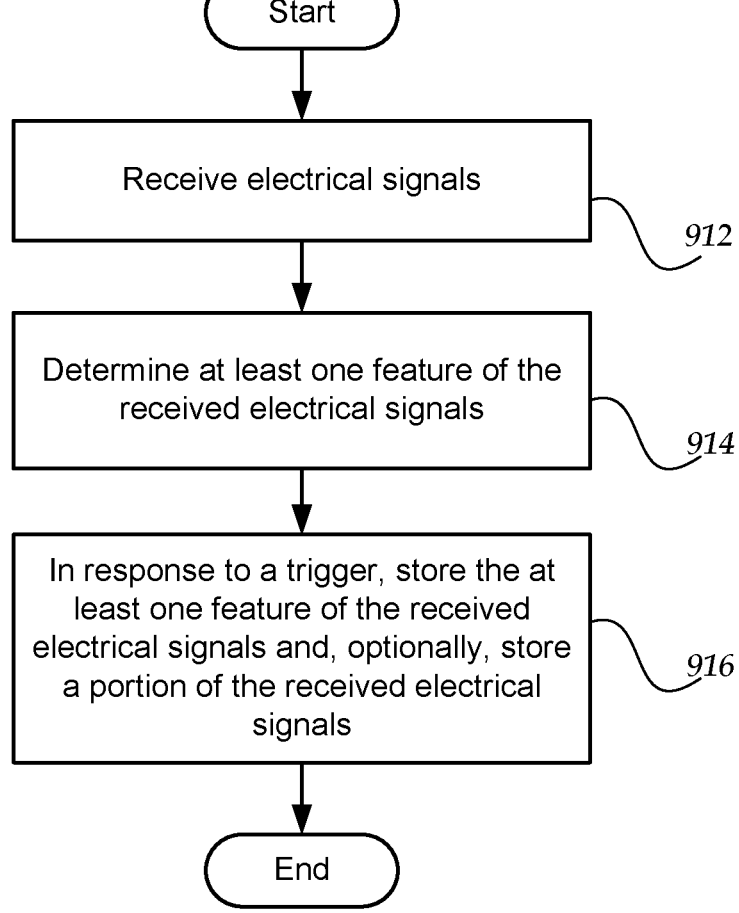
FIG. 9 is a flowchart of one embodiment of a method of storing features of electrical signals on an implantable device.

FIG. 9 is a flowchart of one embodiment of a method of storing features of electrical signals on an implantable device, such as IPG 14 (FIG. 1). In step 912, electrical signals from the tissue of a patient are received by the implantable device. In at least some embodiments, the electrical signals are sensed using electrodes on a lead coupled the implantable device, although other sensing arrangements can also be used. The electrical signals may be sensed continuously or intermittently or in response to a trigger.

In step 914, at least one feature of the received electrical signals is determined. Examples of such features are described above. In at least some embodiments, the determination can be performed by a feature extraction engine of the implantable device. Optionally, the determination of the at least one feature is performed only in response to a trigger. In other embodiments, the at least one feature may be determined continuously or intermittently.

In step 916, in response to a trigger, the at least one feature of the received electrical signals is stored. In some embodiments that utilize a trigger to initiate the determination, his trigger may the same trigger that initiated the determination of the at least one feature. In at least some embodiments, a portion of the received electrical signals can be stored in response to the trigger just as described in step 804 above. In at least some embodiments, this step can be performed by a storage engine of the implantable device.

Figure 10:
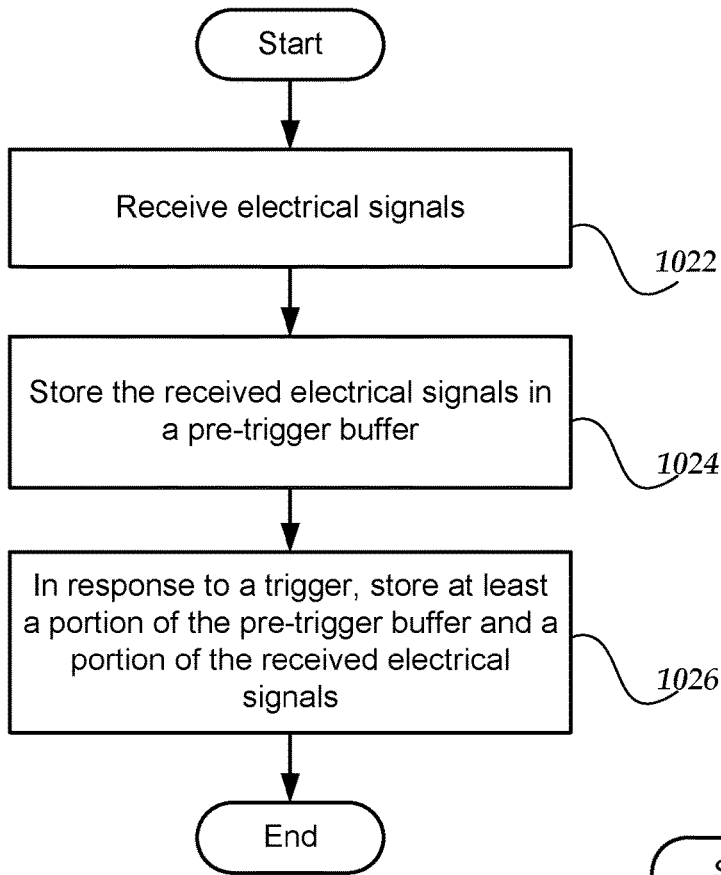
FIG. 10 is a flowchart of another embodiment of a method of storing electrical signals on an implantable device.

FIG. 10 is a flowchart of another embodiment of a method of storing electrical signals on an implantable device, such as IPG 14 (FIG. 1). In step 1022, electrical signals from the tissue of a patient are received by the implantable device. In at least some embodiments, the electrical signals are sensed using electrodes on a lead coupled the implantable device, although other sensing arrangements can also be used. The electrical signals may be sensed continuously or intermittently.

In step 1024, the received electrical signals are stored in a pre-trigger buffer which is overwritten as new electrical signals are received. This storage allows for the capture of electrical signals immediately preceding the trigger because they are stored in the pre-trigger buffer.

In step 1026, in response to a trigger, at least a portion of the pre-trigger buffer and a portion of the received electrical signals are stored. This step is similar to step 804 except that the portion of the pre-trigger buffer is also stored. It will be recognized that the method illustrated in FIG. 9 can also be modified by including step 1024 and, in step, 916 including the storing of at least a portion of the pre-trigger buffer. In at least some embodiments, some or all of the steps can be performed by a storage engine of the implantable device.

Figure 11:
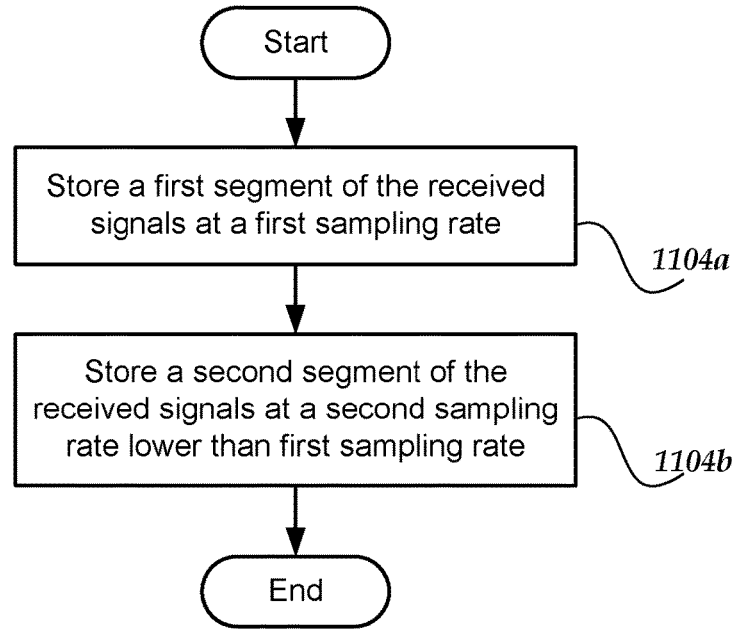
FIG. 11 is a flowchart of yet another embodiment of a method of storing electrical signals on an implantable device.

FIG. 11 is a flowchart of one embodiment of at least a portion of the storage steps 804, 916, and 1026. In step 1104a, a first segment of the received signals is stored at a first sampling rate. In step 1104b, a second segment of the received signals is stored at a second sampling rate that is lower than the first sampling rate. Often the electrical signals vary more immediately after a trigger than later in time and so using a lower sampling rate can reduce the space needed for storage of the second segment without significantly reducing the useful information that is stored. In at least some instances of ESG signals recorded after stimulation is delivered, the first few milliseconds after the stimulus begins may contain the neural response or evoked compound action potential, while after several milliseconds, the evoked response is not present and only spontaneous responses and noise of typically lower magnitude which can be recorded at lower sampling rates.

In other embodiments, as an alternative to, or in addition to, the reduction in sampling rate, a reduction in amplitude range can be made between the first and second segments. In at least some embodiments, a third segment (or fourth, fifth, or more additional segments) can be utilized with decreasing sampling rate or amplitude range. In at least some embodiments, some or all of the steps can be performed by a storage engine of the implantable device.

It will be understood that each block of the flowchart illustration, and combinations of blocks in the flowchart illustration and methods disclosed herein, can be implemented by computer program instructions. In addition, the feature extraction engine, storage engine, visualization engine, and storage programming engine may be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the invention and its use. Since many embodiments of the invention can be made without departing from the spirit and scope of the invention, the invention also resides in the claims hereinafter appended.

What is claimed as new and desired to be protected by Letters Patent of the United States is:

1. An implantable device, comprising:
   a memory; and
   a processor coupled to the memory and configured to perform actions, comprising:
      receiving electrical signals from tissue of a patient; and
      in response to each of a plurality of triggers, storing a portion of the received electrical signals, occurring after the trigger and extending for a limited duration, in the memory on a first-in-first-out basis, wherein the limited duration is divided into at least a first segment and a second segment, wherein storing the portion of the received electrical signals comprises storing a first portion of the received electrical signals during the first segment at a first sampling rate and storing a second portion of the received electrical signals during the second segment at a second sampling rate that is lower than the first sampling rate.

2. The implantable device of claim 1, wherein the trigger comprises a user-initiated trigger or a scheduled trigger.

3. The implantable device of claim 1, wherein the trigger comprises either 1) the electrical signals exceeding a threshold condition or 2) the electrical signals meeting a threshold condition.

4. The implantable device of claim 1, wherein the trigger comprises the electrical signals failing to meet a threshold condition.

5. The implantable device of claim 1, wherein the limited duration is predetermined.

6. The implantable device of claim 1, wherein the actions further comprise storing the received electrical signals in a pre-trigger buffer of the memory and, in response to the trigger, storing at least a portion of the pre-trigger buffer in the memory with the stored portion of the received electrical signals occurring after the trigger.

7. The implantable device of claim 1, wherein the implantable device is an implantable pulse generator, the implantable device further comprising a lead comprising electrodes, wherein receiving electrical signals comprises receiving electrical signals through at least one electrode of the lead.

8. A system, comprising:
   the implantable device of claim 1; and
   a programming device configured for user programming of one or more parameters or triggers relating to the storage in the memory of the implantable device.

9. A method of storing electrical signals from tissue of a patient, the method comprising:
   receiving electrical signals from tissue of a patient; and in response to each of a plurality of triggers, storing in a memory of an implantable device a portion of the received electrical signals, occurring after the trigger and extending for a limited duration, on a first-in-first-out basis, wherein the limited duration is divided into at least a first segment and a second segment, wherein storing the portion of the received electrical signals comprises storing a first portion of the received electrical signals during the first segment at a first sampling rate and storing a second portion of the received electrical signals during the second segment at a second sampling rate that is lower than the first sampling rate.

10. The method of claim 9, further comprising storing the received electrical signals in a pre-trigger buffer of the memory and, in response to the trigger, storing at least a portion of the pre-trigger buffer in the memory with the stored portion of the received electrical signals occurring after the trigger.

11. An implantable device, comprising:
a memory; and
a processor coupled to the memory and configured to perform actions, comprising:
receiving electrical signals from tissue of a patient; and
in response to each of a plurality of triggers, determining at least one feature of the received electrical signals, wherein at least one of the at least one feature is selected from an area under a curve of the received electrical signal; a range of an amplitude of the curve in a defined time window; a length of the curve of the received electrical signal; an energy content of the received electrical signal; a range of a derivative of the received electrical signal in a predefined time window; a time delay of a specified signal peak of the received electrical signal; power of the received electrical signal in a predefined frequency band; variation of a frequency peak with highest energy in the received electrical signal in a predefined frequency band; coherence changes in the received electrical signal; a quality factor for a specified signal peak of the received electrical signal in a predefined time window; full width at half amplitude (FWHM) for a specified signal peak of the received electrical signal in a predefined time window; entropy of the received electrical signal; or spectral entropy of the received electrical signal;
storing the at least one feature in the memory on a first-in-first-out basis; and
in response to each of the plurality of triggers, storing a portion of the received electrical signals, occurring after the trigger and extending for a limited duration, in the memory on a first-in-first-out basis, wherein the limited duration is divided into at least a first segment and a second segment, wherein storing the portion of the received electrical signals comprises storing a first portion of the received electrical signals during the first segment at a first sampling rate and storing a second portion of the received electrical signals during the second segment at a second sampling rate that is lower than the first sampling rate.

12. The implantable device of claim 11, wherein the trigger comprises a user-initiated trigger or a scheduled trigger.

13. The implantable device of claim 11, wherein the trigger comprises either 1) the electrical signals exceeding a threshold condition, 2) the electrical signals meeting a threshold condition, or 3) the electrical signals failing to meet a threshold condition.

14. The implantable device of claim 11, wherein the actions further comprise storing the received electrical signals in a pre-trigger buffer of the memory and, in response to the trigger, storing at least a portion of the pre-trigger buffer in the memory with the stored portion of the received electrical signals occurring after the trigger.

15. The implantable device of claim 11, wherein the implantable device is an implantable pulse generator, the implantable device further comprising a lead comprising electrodes, wherein receiving electrical signals comprises receiving electrical signals through at least one electrode of the lead.

16. A method of storing electrical signals from tissue of a patient in the implantable device of claim 11, the method comprising:
receiving electrical signals from tissue of a patient; and
in response to each of a plurality of triggers, determining at least one feature of the received electrical signals; and
storing the at least one feature in the memory of the implantable device on a first-in-first-out basis.

17. The method of claim 16, further comprising storing the received electrical signals in a pre-trigger buffer of the memory and, in response to the trigger, storing at least a portion of the pre-trigger buffer in the memory with the stored portion of the received electrical signals occurring after the trigger.

18. A system, comprising:
the implantable device of claim 11; and
a programming device configured for user programming of one or more parameters or triggers relating the storage in the memory of the implantable device.

* * * * *